United States Patent
Uribe et al.

(10) Patent No.: US 10,945,933 B2
(45) Date of Patent: Mar. 16, 2021

(54) COMPOSITIONS SUITABLE FOR STYLING HAIR WHICH COMPRISE SALTS AND POLYGLYCERYL ESTERS

(71) Applicant: L'OREAL, Paris (FR)

(72) Inventors: Santiago Uribe, Butler, NJ (US); Aziza Suleiman, Paterson, NJ (US); Anand Mahadeshwar, Scotch Plains, NJ (US); Vanessa Decarlo, Roselle Park, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/445,347

(22) Filed: Feb. 28, 2017

(65) Prior Publication Data
US 2018/0243191 A1    Aug. 30, 2018

(51) Int. Cl.
| | | |
|---|---|---|
| *A61K 8/39* | (2006.01) | |
| *A61K 8/23* | (2006.01) | |
| *A61K 8/19* | (2006.01) | |
| *A61Q 5/06* | (2006.01) | |

(52) U.S. Cl.
CPC .................. *A61K 8/39* (2013.01); *A61K 8/19* (2013.01); *A61K 8/23* (2013.01); *A61Q 5/06* (2013.01); *A61K 2800/33* (2013.01)

(58) Field of Classification Search
CPC . A61Q 5/02; A61Q 19/00; A61Q 5/12; A61K 8/04
See application file for complete search history.

(56) References Cited

U.S. PATENT DOCUMENTS

| | | | | | |
|---|---|---|---|---|---|
| 5,478,490 | A | * | 12/1995 | Russo | ...................... A61K 8/39 424/70.12 |
| 6,620,855 | B2 | * | 9/2003 | Lorant | .................... A61K 8/046 424/45 |
| 7,115,254 | B1 | * | 10/2006 | Brandt | ................. A61K 8/8182 424/70.11 |
| 2008/0020004 | A1 | * | 1/2008 | Birkel | .................... A61K 8/046 424/401 |
| 2010/0111884 | A1 | * | 5/2010 | Acker | .................... A61K 8/046 424/60 |

FOREIGN PATENT DOCUMENTS

JP     WO 2011/052613     *  5/2012  ............... A61K 8/64

* cited by examiner

*Primary Examiner* — Anna R Falkowitz
(74) *Attorney, Agent, or Firm* — Polsinelli PC

(57) ABSTRACT

Provided are compositions suitable as hair styling compositions. Said compositions may comprise (a) at least one salt selected from the group consisting of sodium chloride, magnesium sulfate, calcium chloride, calcium phosphate and combinations thereof; and (b) at least one polyglyceryl ester having a structure represented by:

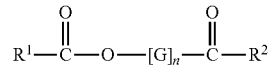

wherein: $R^1$ and $R^2$ are each independently an alkenyl group having 9-21 carbon atoms and at least one unsaturated carbon-carbon bond, G is $CH_2$—$CH(OH)$—$CH_2O$, and n ranges from 1 to 15. Also provided are kits and methods of using said compositions.

15 Claims, No Drawings

COMPOSITIONS SUITABLE FOR STYLING HAIR WHICH COMPRISE SALTS AND POLYGLYCERYL ESTERS

TECHNICAL FIELD

The present disclosure generally relates to compositions and methods for treating keratinous substrates. More particularly, the present disclosure relates to compositions and methods suitable for styling hair.

BACKGROUND

Consumers desire new multi-functional hair products that can impart good styling benefits to hair and impart certain cosmetic characteristic to the hair. Such products should be pleasing to the senses, have innovative, interesting and/or pleasing textures, without loss in functional performance.

Traditional hair styling products on the cosmetic market appear in various forms. They range anywhere from solutions, foams, gels, creams, waxes, mousses, sprays, serums, to aerosols and can impart a variety of levels of protection to the hair depending on the state of the hair and the components of the product. Such products are often sticky or tacky upon application and once dry, may become stiff and/or "crunchy" (i.e. the film is hard and brittle resulting in a crunching feel or sound when the hair is touched), which is undesirable for many consumers. For example, one recent trend is the use of salt sprays, which are used to recreate the texturizing effect that ocean water has on hair. Many of these sprays contain sodium chloride to mimic ocean water. However, these sprays (much like ocean water itself) also leave the hair feeling overly stiff, rough and gritty.

Thus there is an ongoing need for hair styling compositions which impart desired styling benefits but also good sensorial properties.

SUMMARY

One aspect of the invention pertains to a composition comprising:
a. at least one salt selected from the group consisting of sodium chloride, magnesium sulfate, calcium chloride, calcium phosphate and combinations thereof; and
b. at least one polyglyceryl ester having a structure represented by:

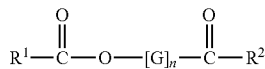

wherein:
$R^1$ and $R^2$ are each independently an alkenyl group having 9-21 carbon atoms and at least one unsaturated carbon-carbon bond,
G is $CH_2$—CH(OH)—$CH_2$O, and
n ranges from 1 to 15.

In one or more embodiments, the at least one salt is selected from the group consisting of sodium chloride, magnesium sulfate, and combinations thereof. In some embodiments, n is 10. In one or more embodiments, $R^1$ and $R^2$ are alkenyl groups having 17 carbon atoms. In some embodiments, the at least one polyglyceryl ester comprises a polyglyceryl dioleate ester. In one or more embodiments, the polyglyceryl dioleate ester comprises polyglyceryl-10 dioleate. In some embodiments, the composition further comprises a cosmetically suitable additive. In one or more embodiments, the composition further comprises about 60-95% by weight of the composition of water. In some embodiments, the at least one salt is present in an amount of about 4 to 20% by weight of the composition. In one or more embodiments, the at least one polyglyceryl ester is present in an amount of about 0.4 to 5.0% by weight of the composition. In some embodiments, the composition does not comprise a surfactant other than the polyglyceryl ester. In one or more embodiments, the composition does not comprise sodium or ammonium lauryl sulfate. In some embodiments, the composition has a viscosity of greater than about 0 to about 150 cP at 20° C.

Another aspect of the invention pertains to a hair styling composition comprising:
a. water;
b. magnesium sulfate;
c. sodium chloride; and
d. a polyglyceryl dioleate ester.

In one or more embodiments, the polyglyceryl dioleate ester comprises polyglyceryl-10 dioleate. In some embodiments, the composition comprises:
a. about 60-95% by weight of the composition of water;
b. about 2 to 9% by weight of the composition of magnesium sulfate;
c. about 3 to 11% by weight of the composition of sodium chloride; and
d. about 0.4 to 5.0% by weight of the composition of polyglyceryl-10 dioleate.

A third aspect of the invention pertains to a kit comprising any of the compositions described above.

A fourth aspect of the invention pertains to a method of styling hair. In one or more embodiments, the method comprises applying to the hair a composition comprising:
a. at least one salt selected from the group consisting of sodium chloride, magnesium sulfate, calcium chloride, calcium phosphate and combinations thereof; and
b. at least one polyglyceryl ester having a structure represented by:

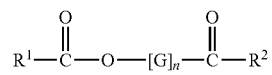

wherein:
R1 and R2 are each independently an alkenyl group having 9-21 carbon atoms and at least one unsaturated carbon-carbon bond,
G is CH2-CH(OH)—CH2O, and
n ranges from 1 to 15
to hair.

In one or more embodiments, applying the composition comprises spraying the composition onto the hair. In some embodiments, applying the composition comprises spraying the composition onto the hair. In one or more embodiments, the at least one polyglyceryl ester comprises a polyglyceryl dioleate ester.

DETAILED DESCRIPTION

Other than in the operating examples, or where otherwise indicated, all numbers expressing quantities of ingredients and/or reaction conditions are to be understood as being modified in all instances by the term "about" which can encompass ±10%, ±8%, ±6%, ±5%, +4%, +3%, +2%, +1%, or +0.5%.

All numbers expressing pH values are to be understood as being modified in all instances by the term "about" which encompasses up to ±3%.

"At least one" as used herein means one or more and thus includes individual components as well as mixtures/combinations.

The term "substantially free of (a component)" as defined herein means that the system or composition contains no appreciable amount of the component, for example, no more than about 1% by weight, no more than about 0.5% by weight, or no more than about 0.3% by weight, such as no more than about 0.1% by weight, based on the weight of the composition.

The term "free" or "completely free of (a component)" as defined herein means that the composition does not contain the component in any measurable degree by standard means.

The term "hair styling" composition refers to compositions which are able to change the shape of the hair either with or without mechanical shaping. In some embodiments, such compositions temporarily change the shape of the hair. Compositions It has been surprisingly discovered that certain compositions, which are suitable as hair styling compositions, impart a desirable texturizing effect (e.g., increase curl definition, shine, discipline and frizz control) while still maintaining good sensorial properties (i.e., softness). In some embodiments, the texturizing effect mimics the wave texture imparted by exposure of hair to ocean water. However, unlike ocean water or even commercially available salt hair sprays, the compositions described herein do not impart an undesirable gritty, stiff or coarse texture to the hair. While not wishing to be bound to any particular theory, it is thought that the addition of certain polyglyceryl esters prevents the gritty texture associated with the salt in salt sprays. The addition of said polyglyceryl ester even allows for relatively high amounts of salt, thereby increasing texturizing effect compared to conventional salt sprays.

Accordingly, one aspect of the invention pertains to a composition comprising
 a. at least one salt selected from the group consisting of sodium chloride, magnesium sulfate, calcium chloride, calcium phosphate and combinations thereof; and
 b. at least one polyglyceryl ester having a structure represented by formula (I):

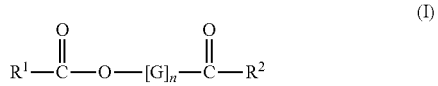

wherein:
 $R^1$ and $R^2$ are each independently an alkenyl group having 9-21 carbon atoms and at least one unsaturated carbon-carbon bond,
 G is $CH_2$—$CH(OH)$—$CH_2O$, and
 n ranges from 1 to 15.

The at least one salt may be selected from the group consisting of sodium chloride, magnesium sulfate, calcium chloride, calcium phosphate and combinations thereof. In further embodiments, the at least one salt comprises sodium chloride, magnesium sulfate, and combinations thereof. In even further embodiments, the at least one salt comprises a mixture of sodium chloride and magnesium sulfate.

The at least one salt may be about 4, 5, 6, 7, 8, 9, 10, 11 or 12 to 13, 14, 15, 16, 17, 18, 19 or 20% by weight of the composition. In further embodiments, the at least one salt is present in an amount of about 12% by weight of the composition. The above amounts pertain to the total amount of all salts present in the composition.

If there is more than one salt present in the composition, then such salts may be present in differing amounts, provided that that total ranges from about 4 to about 20% by weight of the total composition. For example, some compositions may comprise both sodium chloride and magnesium sulfate. In such compositions, sodium chloride may be present in an amount ranging from about 1, 2, 3, 4, 5, 6, 7, 8, 9, 10, 11 or 12 to 8, 9, 10, 11, 12, 13, 14, 15, 16, 17, 18, or 19% by weight of the composition. Similarly, the magnesium sulfate may also be present in an amount ranging from about 1, 2, 3, 4, 5, 6, 7, 8, 9, 10, 11 or 12 to 8, 9, 10, 11, 12, 13, 14, 15, 16, 17, 18, or 19% by weight of the composition, provided that that total ranges from about 4 to about 20% by weight of the total composition. In some embodiments, the at least one salt comprises about 2, 3, 4, or 5 to 5, 6, 7, 8, or 9% by weight of the composition of magnesium sulfate and 3, 4, 5, 6 or 7 to 7, 8, 9, 10, or 11% by weight of the composition of sodium chloride.

As stated above, the at least one polyglyceryl ester having a structure represented by formula (I):

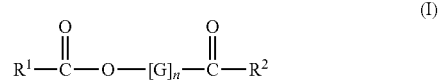

wherein:
 $R^1$ and $R^2$ are each independently an alkenyl group having 9-21 carbon atoms and at least one unsaturated carbon-carbon bond,
 G is $CH_2$—$CH(OH)$—$CH_2O$, and
 n ranges from 1 to 15.

Polyglyceryl esters are readily obtained by the esterification of fatty acids with the hydroxyl groups of polyglycerol. The contribution of the fatty acid is represented by the R groups in formula (I). In some embodiments, $R^1$ and $R^2$ are the same. In other embodiments, $R^1$ and $R^2$ are different. Since $R^1$ and $R^2$ are each independently an alkenyl group having 9-21 carbon atoms and at least one unsaturated carbon-carbon bond, then the fatty acids are those having 10-22 carbon atoms and are at least mono-unsaturated. One non-limiting example of such a fatty acid is oleic acid. When oleic acid is utilized to produce the polyglyceryl ester, then $R^1$ and/or $R^2$ have 17 carbon atoms and one unsaturated carbon-carbon bond. Where $R^1$ and $R^2$ are both formed from oleic acid, the polyglyceryl esters are polyglyceryl dioleate esters.

The number of glycerol units (represented by G in formula (I)) in the polyglyceryl esters may range from 1 to 15 (corresponding to the variable n). Variable n can range from 1, 2, 3, 4, 5, 6, 7, 8, 9 or 10 to 10, 11, 12, 13, 14 or 15. In one or more embodiments, n may be 1, 2, 3, 4, 5, 6, 7, 8, 9, 10, 11, 12, 13, 14, or 15. In further embodiments, n is 10.

In some embodiments, the polyglyceryl ester is a polyglyceryl dioleate ester. In further embodiments, the polyglyceryl dioleate ester comprises polyglyceryl-1 dioleate, polyglyceryl-2 dioleate, polyglyceryl-3 dioleate, polyglyceryl-4 dioleate, polyglyceryl-5 dioleate, polyglyceryl-6 dioleate, polyglyceryl-7 dioleate, polyglyceryl-8 dioleate, polyglyceryl-9 dioleate, polyglyceryl-10 dioleate, polyglyceryl-11 dioleate, polyglyceryl-12 dioleate, polyglyceryl-13 dioleate, polyglyceryl-14 dioleate, or polyglyceryl-15 dioleate. In yet further embodiments, the polyglyceryl dioleate ester comprises polyglyceryl-10 dioleate.

The at least one polyglyceryl ester may be present in the composition in an amount of about 0.4 to 5.0% by weight of the composition. In further embodiments, the at least one polyglyceryl ester is present in amount of from about 0.4, 0.5, 0.6, 0.7, 0.8, 0.9, 1.0, 1.5, 2.0, 2.5, 3.0, 4.0 to about 0.6, 0.7, 0.8, 0.9, 1.0, 1.5, 2.0, 2.5, 3.0, 4.0 or 5.0% by weight of the composition. In some embodiments, the at least one polyglyceryl ester is present in an amount of about 0.4, 0.5, 0.6, 0.7, 0.8, 0.9, 1.0% by weight of the composition.

In one or more embodiments, the compositions of the invention comprise water. The water may be present in an amount of about 60-95% by weight of the composition of water. In further embodiments, the water is present in an amount of about 60, 65, 70, 75, 80, or 85 to about 85, 90 or 95% by weight of the composition. In further embodiments, the water is present in an amount of about 80-90% by weight of the composition.

In one or more embodiments, the hair styling compositions may be "leave-on" or "leave-in" hair-care compositions. As suggested by the term "leave-on hair styling compositions," these compositions are formulated so that they can remain on the hair for extended periods of time, i.e., the compositions are applied to the hair, for example, during styling of the hair and allowed to remain for one or more hours, or one or more days before being removed, for example, by washing. In other words, the leave-on compositions are applied to the hair and allowed to remain on the hair without immediate rinsing or removal. The leave-on hair-care compositions may be applied to the hair, for example, after shampooing, before or during the styling process. The hair may be wet, damp, or already dry when the hair-care composition is applied to the hair. In some cases, the leave-on hair-care composition may be applied to wet or damp hair after which the hair is blow dried and styled. In other cases, the hair may be previously dried and the hair-care composition is applied to dry hair, in order to treat, shape, or style the hair.

Other Additives

In one or more embodiments, the compositions described herein further comprise a cosmetically suitable additive.

However, the hair styling compositions of the instant disclosure are unique in that they do not require synthetic polymers such as synthetic film-forming polymers. In fact, the hair styling compositions do not necessarily require any synthetic ingredients. In some cases, synthetic film-forming polymer or synthetic polymer may be included but in other cases, they may be excluded. The term "synthetic polymer" (or "synthetic film-forming polymer") means a polymer, which is purely synthetic, or not of natural origin, especially those polymers, which are made by radical polymerization of ethylenically unsaturated monomers or by polycondensation. The term "natural polymer" means a polymer of natural origin, which includes those that have been subsequently chemically or physically modified (but retains at least 50% of its molecular structure from the original natural source). In particular, the term "natural original ingredient" refers to one of the following:

(1) an ingredient which remains unchanged from its natural state; or
(2) an ingredient which has undergone chemical or other processing which modifies it from its natural state but which retains at least 50% of its molecular structure from the original natural source.

In general, a natural ingredient may be processed to improve its stability, efficacy and/or safety for use in hair styling products. The degree of processing varies for each ingredient, but at the end only an ingredient that retains at least 50% of its molecular structure from the original natural source is considered natural origin. In some cases, the hair-care compositions of the instant disclosure are "natural hair-care compositions." A "natural hair-care compositions" is a hair-care composition comprising only "natural origin ingredients," as defined above.

Non-limiting examples of synthetic film-forming polymers (which in some cases may be excluded from the instant hair-care compositions) include non-ionic hair-fixing polymers (e.g., copolymerizates of vinyl pyrrolidone and vinyl acetate, terpolymers of vinyl pyrrolidone, vinyl acetate and vinyl propionate, polyacrylamides, polyvinyl alcohols and polyethylene glycol/polypropylene glycol copolymers. Polyvinyl pyrrolidone, polyvinyl caprolactam and their copolymers with at least one further nonionic monomer, for example, polyvinylpyrrolidone/vinyl acetate copolymers) and anionic hair-fixing polymers such as synthetic homo- or copolymers with neutralizable monomer units containing acid groups, which are copolymerizable with comonomers, if necessary, which contain no acid groups. The acid groups may include —COOH, —SO$_3$H, —OSO$_3$H, —OPO$_2$H, —PO$_3$H$_2$. The acid groups can be unneutralized, or partially or completely neutralized.

Furthermore, the leave-in hair styling compositions do not require silicones (silicone and silicone containing materials). Non-limiting examples of silicones (which may optionally excluded from the instant hair-care compositions) include dimethicone, dimethiconol, amodimethicone, cyclomethicones, amino-modified silicones, and polyether-modified silicones.

Additionally, as one or more embodiments of the instant disclosure are styling compositions, the composition will generally be free or substantially free of cleansing surfactants. Non-limiting examples of cleansing surfactants that may be excluded include anionic cleansing surfactants, for example, sulfates, carboxylates, sulfonates, and phosphates. Similarly, betaines may be excluded. In one or more embodiments, the composition does not comprise a surfactant other than the polyglyceryl ester. In further embodiments, the composition does not comprise sodium or ammonium lauryl sulfate.

Cationic Surfactants

Although no surfactants apart from the polyglyceryl ester are required, in one or more embodiments, the composition comprises a cationic surfactant. The term "cationic surfactant" means a surfactant that is positively charged when it is contained in the composition according to the disclosure. This surfactant may bear one or more positive permanent charges or may contain one or more functions that are cationizable in the composition according to the disclosure.

Non-limiting examples of cationic surfactants include behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

Anionic Surfactants

Although no surfactants apart from the polyglyceryl ester are required, in one or more embodiments, the composition comprises an anionic surfactant. The term "anionic surfactant" means a surfactant comprising, as ionic or ionizable groups, only anionic groups. These anionic groups are chosen preferably from the groups $CO_2H$, $CO_2^-$, $SO_3H$, $SO_3^-$, $OSO_3H$, $OSO_3^-$ $O_2PO_2H$, $O_2PO_2H$ and $O_2PO_2^{2-}$.

The anionic surfactant(s) that may be used may be alkyl sulfates, alkyl ether sulfates, alkylamido ether sulfates, alkylaryl polyether sulfates, monoglyceride sulfates, alkylsulfonates, alkylamide sulfonates, alkylarylsulfonates, alpha-olefin sulfonates, paraffin sulfonates, alkylsulfosuccinates, alkyl ether sulfosuccinates, alkylamide sulfosuccinates, alkyl sulfoacetates, acylsarcosinates, acylglutamates, alkylsulfosuccinamates, acylisethionates and N-acyltaurates, salts of alkyl monoesters and polyglycoside-polycarboxylic acids, acyllactylates, salts of D-galactoside uronic acids, salts of alkyl ether carboxylic acids, salts of alkyl aryl ether carboxylic acids, and salts of alkylamido ether carboxylic acids; or the non-salified forms of all of these compounds, the alkyl and acyl groups of all of these compounds containing from 6 to 24 carbon atoms and the aryl group denoting a phenyl group. Some of these compounds may be oxyethylenated and then preferably comprise from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfo succinates.

When the anionic surfactant(s) are in salt form, they may be chosen especially from alkali metal salts such as the sodium or potassium salt and preferably the sodium salt, ammonium salts, amine salts and in particular amino alcohol salts, or alkaline-earth metal salts such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts. Alkali metal or alkaline-earth metal salts and in particular the sodium or magnesium salts may be used.

Use is also made of ($C_6$-$C_{24}$)alkyl sulfates, ($C_6$-$C_{24}$)alkyl ether sulfates, which are optionally ethoxylated, comprising from 2 to 50 ethylene oxide units, and mixtures thereof, in particular in the form of alkali metal salts or alkaline-earth metal salts, ammonium salts or amino alcohol salts. More preferentially, the anionic surfactant(s) are chosen from ($C_{10}$-$C_{20}$)alkyl ether sulfates, and in particular sodium lauryl ether sulfate containing 2.2 mol of ethylene oxide.

Amphoteric Surfactants

Although no surfactants apart from the polyglyceryl ester are required, in one or more embodiments, the composition comprises an amphoteric surfactant. Amphoteric surfactants useful in the cosmetic compositions disclosed herein may be chosen from betaines, sultaines, amphoacetates, amphoproprionates, and mixtures thereof. More typically, betaines and amphoproprionates are used, and most typically betaines. Betaines which can be used in the current compositions include those having the formulas below:

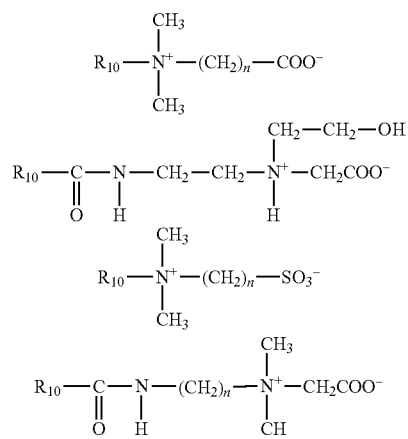

wherein $R^{10}$ is an alkyl group having 8-18 carbon atoms; and n is an integer from 1 to 3.

Particularly useful betaines include, for example, coco betaine, cocoamidopropyl betaine, lauryl betaine, laurylhydroxy sulfobetaine, lauryldimethyl betaine, cocoamidopropyl hydroxysultaine, behenyl betaine, capryl/capramidopropyl betaine, lauryl hydroxysultaine, stearyl betaine, and mixtures thereof. Typically, the at least one betaine compound is selected from the group consisting of coco betaine, cocoamidopropyl betaine, behenyl betaine, capryl/capramidopropyl betaine, lauryl betaine, and mixtures thereof, and more typically coco betaine.

Hydroxyl sultaines useful in the compositions of the invention include the following

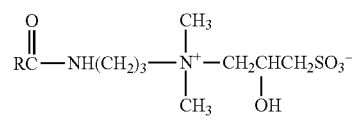

wherein

R is an alkyl group having 8-18 carbon atoms.

Useful alkylamphoacetates include those having the formula

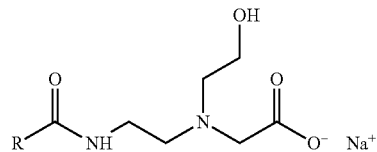

wherein

R is an alkyl group having 8-18 carbon atoms.

useful alkyl amphodiacetates include those having the formula

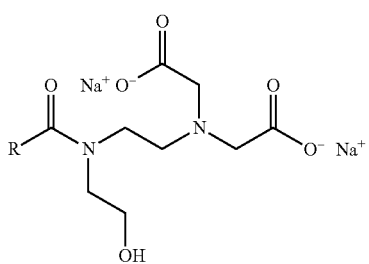

wherein

R is an alkyl group having 8-18 carbon atoms.

The amphoteric surfactants of the present disclosure may be optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group.

Non-Ionic Surfactants

Although no surfactants apart from the polyglyceryl ester are required, in one or more embodiments, the composition comprises a non-ionic surfactant. Nonionic surfactants are compounds well known in themselves (see, e.g., in this regard, "Handbook of Surfactants" by M. R. Porter, Blackie & Son publishers (Glasgow and London), 1991, pp. 116-178), which is incorporated herein by reference in its entirety.

The nonionic surfactant can be, for example, selected from alcohols, alpha-diols, alkylphenols and esters of fatty acids, these compounds being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and mixtures thereof.

The nonionic surfactants may preferably be chosen from polyoxyalkylenated or polyglycerolated nonionic surfactants. The oxyalkylene units are more particularly oxyethylene or oxypropylene units, or a combination thereof, and are preferably oxyethylene units.

According to one of the embodiments according to the present invention, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

As glyceryl esters of fatty acids, glyceryl stearate (glyceryl mono-, di- and/or tristearate) (CTFA name: glyceryl stearate) or glyceryl ricinoleate and mixtures thereof can in particular be cited.

As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited.

Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEG1N by Goldschmidt (CTFA name: glyceryl stearate SE), can also be used.

Cationic Conditioning Agents

The hair styling composition may include one or more cationic conditioning agents. The cationic conditioning agents that may be employed in the compositions of the present disclosure can be a monoalkyl quaternary amine, such as stearyltrimonium chloride, soyatrimonium chloride or coco-ethyldimonium ethosulfate. Other suitable cationic conditioning agents include, but are not limited to, behentrimonium chloride, dialkyl quaternary amines, such as dicetyldimonium chloride, dicocodimethyl ammonium chloride or distearyldimethyl ammonium chloride; and polyquaternium compounds, such as Polyquaternium-6, Polyquaternium-22 or Polyquaternium-5.

For example, cationic conditioning agents may be chosen from polyquaterium-10 (also called quaternized polyhydroxyethyl cellulose), cetrimonium chloride (also called cetyl trimethyl ammonium chloride, CTAC), behentrimonium chloride (also known as docosyl trimethyl ammonium chloride), behentrimonium methosulfate, steartrimonium chloride, stearalkonium chloride, dicetyldimonium chloride, hydroxypropyltrimonium chloride, cocotrimonium methosulfate, olealkonium chloride, steartrimonium chloride, babassuamidopropalkonium chloride, brassicamidopropyl dimethylamine, Quaternium-91, Salcare/PQ-37, Quaternium-22, Quaternium-87, Polyquaternium-4, Polyquaternium-6, Polyquaternium-11, Polyquaternium-44, Polyquaternium-67, amodimethicone, lauryl betaine, Polyacrylate-1 Crosspolymer, steardimonium hydroxypropyl hydrolyzed wheat protein, behenamidopropyl PG-dimonium chloride, lauryldimonium hydroxypropyl hydrolyzed soy protein, aminopropyl dimethicone, Quaterium-8, and dilinoleamidopropyl dimethylamine dimethicone PEG-7 phosphate.

In some instances, the cationic conditioning agents are cationic polymers. The term "cationic polymer" means any polymer comprising at least one cationic group and/or at least one group that may be ionized into a cationic group.

Particularly useful cationic polymers in the present invention include, but are not limited to, polyquaternium-4, polyquaternium-6, polyquaternium-7, polyquaternium-10, polyquaternium-11, polyquaternium-16, polyquaternium-22, polyquaternium-28, polyquaternium-32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, and guar hydroxypropyltrimonium chloride.

Particularly preferred cationic polymers of the present invention include POLYMER JR-125, POLYMER JR-400, Polymer JR-30M hydroxyethyl cellulosic polymers (polyquaternium 10) available from AMERCHOL; JAGUAR C® 13-S, guar hydroxypropyltrimonium chloride, available from Rhodia; and MERQUAT® 100 and 280, a dimethyl dialkyl ammonium chloride (polyquaternium 6) available from Nalco.

The cationic polymer is generally present in an amount of from greater than 0% to about 15%, preferably from about 0.5% to about 10% by weight, and more preferably from about 1% to about 5% by weight, based on the total weight of the composition.

Cationic polymers useful herein include polyquaternium 4, polyquaternium 6, polyquaternium 7, polyquaternium 10, polyquaternium 11, polyquaternium 16, polyquaternium 22, and polyquaternium 32. Cationic polymers useful in the present invention include, but are not limited to, polyquaternium 4, polyquaternium 6, polyquaternium 7, polyquaternium 10, polyquaternium 11, polyquaternium 16, polyquaternium 22, polyquaternium 28, polyquaternium 32, and guar hydroxypropyltrimonium chloride. Preferred cationic polymers include POLYMER JR-125, POLYMER JR-400, Polymer JR-30M hydroxyethyl cellulosic polymers (polyquaternium 10) available from AMERCHOL; JAGUAR C13-S, guar hydroxypropyltrimonium chloride, available from Rhodia; and MERQUAT 100 and 280, a dimethyl dialkyl ammonium chloride (polyquaternium 6) available from Nalco.

Oils

The hair styling composition may include one or more oils, for example, silicone oils, fluoro oils, hydrocarbon-based oils, etc. The term "oil" means any fatty substance which is in liquid form at room temperature (20-25° C.) and at atmospheric pressure (760 mmHg). Often, at least one of the oils in the cosmetic composition is part of an oily phase. An "oily phase" is a phase comprising at least one oil that may include additional liposoluble and lipophilic ingredients and the fatty substances. The oily phase can be combined with an aqueous phase in an emulsion. Oil that is suitable for use herein may be volatile or non-volatile. The term "volatile oil" relates to oil that is capable of evaporating on contact with the skin or a keratin fiber in less than one hour, at room temperature and atmospheric pressure. The volatile oil(s) are liquid at room temperature and have a non-zero vapor pressure, at room temperature and atmospheric pressure, ranging in particular from 0.13 Pa to 40 000 Pa ($10^{-3}$ to 300 mmHg). The term "non-volatile oil" relates to oil which remains on the skin or the keratin fiber, at room temperature and atmospheric pressure, for at least several hours and which in particular has a vapor pressure of less than $10^{-3}$ mmHg (0.13 Pa).

The cosmetic compositions described herein may comprise one or more silicone oils. The term "silicone oil" relates to oil comprising at least one silicon atom, and especially at least one Si—O group. Non-limiting examples of silicone oils include dimethicone, cyclomethicone, polysilicone-11, phenyl trimethicone, trimethylsilylamodimethicone, and stearoxytrimethylsilane. In some cases, the cosmetic composition includes dimethicone, and optionally additional oils, including additional silicone oils. Typically, the one or more silicone oils is a non-volatile silicon oil. In some embodiments, the silicone oil is polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl) trimethylsiloxysilicates. Other examples of silicone oils that may be mentioned include volatile linear or cyclic silicone oils, especially those with a viscosity 8 centistokes ($8\times10^6$ m$^2$/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

The cosmetic compositions described herein may comprise one or more fluoro oils. The term "fluoro oil" relates to oil comprising at least one fluorine atom. For example, the one or more fluoro oil may be selected from the group consisting of perfluoromethylcyclopentane, perfluoro-1,3-dimethylcyclohexane, dodecafluoropentane, tetradecafluorohexane, bromoperfluorooctyl, nonafluoromethoxybutane, nonafluoroethoxyisobutane and 4-trifluoromethylperfluoromorpholine. Volatile fluoro oils, such as nonafluoromethoxybutane, decafluoropentane, tetradecafluorohexane, dodecafluoropentane, may also be used.

The cosmetic compositions described herein may comprise one or more hydrocarbon-based oils. The term "hydrocarbon-based oil" relates to oil comprising mainly hydrogen and carbon atoms. Hydrocarbon-based oil may be animal hydrocarbon-based oil, plant hydrocarbon-based oil, mineral hydrocarbon-based oil or a synthetic hydrocarbon-based oil.

Further, suitable oil may be a mineral hydrocarbon-based oil, a plant hydrocarbon-based oil, or a synthetic hydrocarbon-based oil. For example, the hydrocarbon-based oil may be a saturated hydrocarbon, an unsaturated hydrocarbon, lipids, triglycerides, a natural oil, and/or a synthetic oil. In some embodiments, the compositions include a synthetic oil selected from the group consisting of hydrogenated polyisobutene and hydrogenated polydecene.

Preservatives

One or more preservatives may be included in the compositions described herein for treating hair. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, ethylenediamine-tetraacetic acid (EDTA), potassium sorbate, and/or grapefruit seed extract, or combinations thereof. More than one preservative may be included in the composition. Other preservatives are known in the cosmetics industries and include salicylic acid, DMDM hydantoin, formaldehyde, chlorphenesin, triclosan, imidazolidinyl urea, diazolidinyl urea, sorbic acid, methylisothiazolinone, sodium dehydroacetate, dehydroacetic acid, quaternium-15, stearalkonium chloride, zinc pyrithione, sodium metabisulfite, 2-bromo-2-nitropropane, chlorhexidine digluconate, polyaminopropyl biguanide, benzalkonium chloride, sodium sulfite, sodium salicylate, citric acid, neem oil, essential oils (various), lactic acid, and vitamin E (tocopherol).

The total amount of the one or more preservatives, when present, may vary. In some cases, the total amount of the one or more preservatives is about 0.01 to about 5 wt. %, about 0.01 to about 4 wt. %, about 0.15 to about 1 wt. %, or about 1 to about 3 wt. %, based on the total weight of the composition.

Suitable components, such as those listed in the instant disclosure (including those listed above), may be included or excluded from the hair styling compositions depending on the specific combination of other components, the form of the compositions, and/or the use of the formulation (e.g., hair spray, cream, paste, conditioner, etc.).

Kits

Another aspect of the invention pertains to a kit comprising any of the compositions described herein. The composition may be packaged in a variety of different containers, such as, for example, a ready-to-use container. Non-limiting examples of useful packaging include tubes, jars, caps, unit dose packages and bottles, including squeezable tubes and bottles. In one or more embodiments, the packaging is a configured to squire, spray or mist a fluid. In further embodiments, the packaging is a spray bottle. In embodiments where the composition is housed in a spray bottle, the composition will have a viscosity appropriate to spray. In some embodiments, the composition has a viscosity of greater than about 0 to about 150 cP at 20° C. In further embodiments, the composition has a viscosity of about 0.1, 0.2, 0.3, 0.4, 0.5, 0.6, 0.7 or 0.8 to about 1, 2, 3, 4, 5, 10, 15, 20, 25, 30, 35, 40, 45, 50, 60, 70, 80, 90, 100, 125 or 150 cP.

Method

Another aspect of the invention pertains to a method of styling (i.e., shaping) hair, for example, human hair, including human hair one an individual's head. For example, the compositions are useful for: (i) improving or retaining curl definition of hair; (ii) imparting humidity resistance to hair; (iii) reducing hair frizz; (iv) controlling hair volume; (v) styling hair; (vi) straightening hair; and (vi) improving the appearance of hair. The method comprises applying to hair any of the compositions described herein. In some embodiments, composition may be applied via spraying the composition to hair. The method may further comprise mechanically styling the hair after applying the composition to the hair. Examples of mechanically styling the hair after application of the composition include, but are not limited to, combing, combing, straightening, curling, applying a styling iron, drying with blow dryer etc.

The composition may then be allowed to remain on the hair, for example, for one or more hours, or one or more days before being removed by a subsequent washing. The composition may be applied to wet, damp, or already dry hair.

Exemplary Embodiments

Any of the embodiments described above may be combined together. In one exemplary embodiment, the hair styling composition comprises
   a. water;
   b. magnesium sulfate;
   c. sodium chloride; and
   d. a polyglyceryl dioleate ester according to Formula (I).

In further embodiments, the polyglyceryl dioleate ester comprises polyglyceryl-10 dioleate.

In further embodiments, the composition comprises
   a. about 60-95% by weight of the composition of water;
   b. about 2 to 9% by weight of the composition of magnesium sulfate;
   c. about 3 to 11% by weight of the composition of sodium chloride; and
   d. about 0.4 to 5.0% by weight of the composition of polyglyceryl-10 dioleate.

In some embodiments, these exemplary embodiments may comprise further additives, such as, for example, preservatives.

The above exemplary embodiments may be housed in a spray bottle packaging. Additionally, these exemplary composition embodiments may be used in a method to style the hair. For example, the compositions may be applied to hair (e.g., sprayed). Then the hair may be subsequently styled using a mechanical means (e.g., applying a curling or straightening iron).

Examples

Implementation of the present disclosure is provided by way of the following examples. The examples serve to illustrate the technology without being limiting in nature.

The ingredient amounts in the composition/formulations described below are expressed in % by weight, based on the total weight of the composition, unless otherwise indicated.

Several different emulsifiers were incorporated into mineral salt formula compositions and subsequently evaluated.

Inventive 1 was composed of the ingredients shown in Table 1. The composition was prepared by simple mixing and dissolution of all powders

TABLE 1

Inventive 1 Composition

| INCI US Name | Concentration |
| --- | --- |
| MAGNESIUM SULFATE | 5 |
| TOCOPHEROL | 0.00025 |
| SODIUM HYDROXIDE | 0.02 |
| POLYGLYCERYL-10 DIOLEATE | 0.49975 |
| PRESERVATIVE | 0.4 |

TABLE 1-continued

Inventive 1 Composition

| INCI US Name | Concentration |
|---|---|
| GLYCERIN | 0.8 |
| SODIUM CHLORIDE | 7 |
| WATER | 86.27 |
| NATURAL EXTRACT | 0.006 |
| DEXTRIN | 0.004 |
| Total: | 100 |

Comparatives 2-6 were prepared in the same way as Inventive 1 except in each a comparative material according to Table 2 was incorporated into the base in place of polyglyceryl-10 dioleate. Comparative 7 is a commercially available salt spray product.

TABLE 2

Summary of Results

| | Surfactant |
|---|---|
| Comparative 2 | Caprylyl/Capryl Glucoside |
| Comparative 3 | Polyglyceryl-6 Dicaprate |
| Comparative 4 | Decyl Glucoside |
| Comparative 5 | Polyglyceryl -10 Laurate |
| Comparative 6 | Glyceryl dibehenate and tribehenin |
| Comparative 7 | None (Commercially available product) |

Inventive 1 and Comparatives 2-7 were tested on mannequin heads. 2 ml of product was sprayed onto clean mannequin head hair and brushed through for optimum distribution. The hair was allowed to air dry and subsequently evaluated for curl formation, dryness, softness, grit, roughness and frizz control. Curl formation was evaluated based on definition and size of curls. Dryness, softness, grit and roughness were evaluated sensorially with touch. Observations were confirmed amongst several evaluators to obtain consensus on evaluations.

The results of each of the compositions is shown below in Table 3:

TABLE 3

Summary of Results

| | Surfactant | Result |
|---|---|---|
| Inventive 1 | Polyglyceryl-10 Dioleate | Hair had good curl definition, shine, frizz control while still found to be soft. |
| Comparative 2 | Caprylyl/Capryl Glucoside | Hair was left dry and rough. |
| Comparative 3 | Polyglyceryl-6 Dicaprate | Hair was given good curl definition but only slightly softer. |
| Comparative 4 | Decyl Glucoside | Hair was left dry and rough. |
| Comparative 5 | Polyglyceryl -10 Laurate | Hair was found to be significantly softer but curl definition was compromised. |
| Comparative 6 | Glyceryl dibehenate and tribehenin | Hair was dull and rough. |
| Comparative 7 | None (Commercially available product) | Hair was had curl formation, beachy waves, and windswept texture. However, also rough, gritty and not soft whatsoever |

As can be seen from the results, only Inventive 1 provided good curl definition, shine and frizz control without making the hair rough. The results are surprising because even surfactants which are chemically similar do not achieve similar results. For example, Comparative 5 also features a polyglyceryl ester with 10 glycerol units like Inventive 1, but Comparative 5 is an ester of lauric acid, whereas Inventive 1 is an ester of oleic acid. Comparative 5 made the hair softer, but did not achieve the curl effect of Inventive 1.

What is claimed is:

1. A composition comprising:
    a. about 2 to 9% by weight of magnesium sulfate;
    b. about 3 to 11% by weight of sodium chloride; and
    c. about 0.4 to 5.0% by weight of a polyglyceryl dioleate ester,
        wherein the composition does not comprise a surfactant other than the polyglyceryl ester and does not comprise terpolymers of vinyl pyrrolidone, and wherein the composition has a viscosity up to about 50 cP at 20° C., and
        wherein the composition provides hair with curl definition, shine, and frizz control, while maintaining softness of the hair.

2. The composition of claim 1, wherein the polyglyceryl dioleate ester comprises polyglyceryl-10 dioleate.

3. The composition of claim 1, wherein the composition further comprises a cosmetically suitable additive.

4. The composition of claim 1, further comprising about 60-95% by weight of the composition of water.

5. The composition of claim 1, wherein the composition has a viscosity up to about 5 cP at 20° C.

6. A hair styling composition consisting of:
    a. water;
    b. magnesium sulfate;
    c. sodium chloride; and
        wherein a total amount of magnesium sulfate and sodium chloride is from about 4 to 20% by weight,
    d. about 0.4 to 5.0% by weight of a polyglyceryl dioleate ester;
    e. one or more preservatives;
    f. optionally, sodium hydroxide;
    g. optionally, one or more natural extracts; and
    h. optionally, dextrin.

7. The composition of claim 6, wherein the polyglyceryl dioleate ester comprises polyglyceryl-10 dioleate.

8. A hair styling composition consisting of:
    a. about 60-95% by weight of the composition of water;
    b. about 2 to 9% by weight of the composition of magnesium sulfate;
    c. about 3 to 11% by weight of the composition of sodium chloride;
    d. about 0.4 to 5.0% by weight of the composition of polyglyceryl-10 dioleate;
    e. one or more preservatives;
    f. sodium hydroxide;
    g. one or more natural extracts; and
    h. dextrin.

9. A kit comprising the composition of claim 1 in a spray bottle.

10. A method of styling hair, the method comprising applying to the hair the composition of claim 1.

11. The method of claim 10, wherein applying the composition comprises spraying the composition onto the hair.

12. A method of styling hair, the method comprising applying to the hair the composition of claim 8.

13. The composition of claim 1, wherein the composition does not comprise vinyl pyrrolidone.

14. The composition of claim 1, wherein the composition does not comprise synthetic film-forming polymers.

15. The composition of claim 1 comprising about 0.4 to 2.0% by weight of the polyglyceryl dioleate ester.

* * * * *